(12) United States Patent
Cosyns et al.

(10) Patent No.: US 6,333,442 B1
(45) Date of Patent: Dec. 25, 2001

(54) PROCESS FOR THE PREPARATION OF AN ALIPHATIC ALKYLATE WITH A HIGH OCTANE NUMBER FROM A C4 CRACKING FRACTION

(75) Inventors: Jean Cosyns, Maule; Blaise Didillon, Rueil Malmaison; Lionel Quicke, Paris, all of (FR)

(73) Assignee: Institut Francais du Petrole (FR)

( * ) Notice: Subject to any disclaimer, the term of this patent is extended or adjusted under 35 U.S.C. 154(b) by 0 days.

(21) Appl. No.: 09/256,185

(22) Filed: Feb. 24, 1999

(30) Foreign Application Priority Data

Feb. 24, 1998 (FR) .................................... 98 02307

(51) Int. Cl.$^7$ ...................................... C07C 2/58
(52) U.S. Cl. .................. 585/332; 585/331; 585/300; 585/304
(58) Field of Search .................. 585/300, 304, 585/331, 332

(56) References Cited

U.S. PATENT DOCUMENTS

| | | | |
|---|---|---|---|
| 2,594,343 | * 4/1952 | Pines | 585/332 |
| 2,904,498 | * 9/1959 | Findlay | 585/302 |
| 3,663,646 | * 5/1972 | Chapman | 585/332 |
| 4,268,701 | 5/1981 | Vu et al. | 585/329 |
| 4,324,938 | * 4/1982 | Cosyns et al. | 585/331 |
| 4,392,002 | * 7/1983 | Cosyns et al. | 585/332 |
| 5,237,115 | * 8/1993 | Makovec et al. | 585/331 |
| 5,998,683 | * 12/1999 | Lattner et al. | 585/317 |

FOREIGN PATENT DOCUMENTS 2436176    4/1980    (FR).

* cited by examiner

*Primary Examiner*—Walter D. Griffin
(74) *Attorney, Agent, or Firm*—Millen, White, Zelano & Branigan, P.C.

(57) ABSTRACT

An aliphatic alkylate with a high octane number is prepared from a C4 catalytic cracking or steam-cracking fraction that contains mainly isobutane, isobutene, butene-1 and butenes-2 by:

(a) hydro-isomerizing said C4 fraction, obtaining a mixture that contains for the most part butenes-2, isobutene and isobutane;

(b) separating, by distillation of the hydro-isomerized fraction, of a butene-2-rich effluent that is collected at the bottom and an isobutane- and isobutene-rich effluent that is collected at the top;

(c) sending said isobutene- and isobutane-rich effluent into a hydrogenation zone that produces an effluent that for the most part contains isobutane;

(d) sending of said butenes-2-rich effluent that is derived from (b) and of said effluent that for the most part contains the isobutane that is derived from (c) into an alkylation zone producing, by addition of isobutane to butenes-2, an isooctane mixture that contains excess isobutane;

(e) separating by distillation of excess isobutane, which comes out at the top, and alkylate with an improved octane number, which comes out at the bottom; and (f) recycling of the excess isobutane that is recovered in (e) upstream from hydrogenation (c) of the top effluent from the distillation of (b).

12 Claims, 1 Drawing Sheet

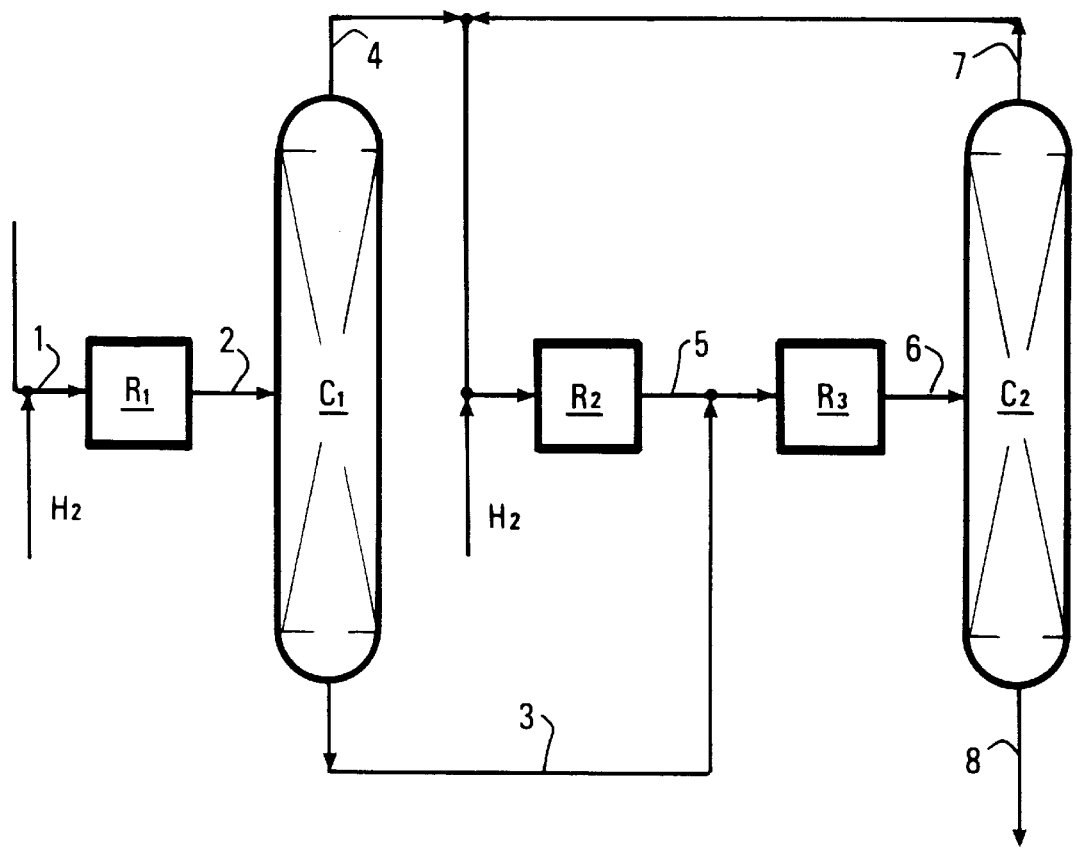

PROCESS FOR THE PREPARATION OF AN ALIPHATIC ALKYLATE WITH A HIGH OCTANE NUMBER FROM A C4 CRACKING FRACTION

SUMMARY OF THE INVENTION

The invention relates to an improved process for the preparation of an aliphatic alkylate with a high octane number from a C4 catalytic cracking or steam-cracking fraction. The isooctane mixture that is obtained can be used as a gasoline component with high octane numbers.

Catalytic cracking, which produces automobile gasoline, also produces a large amount of light hydrocarbons, in particular with 4 carbon atoms. The $C_4$ hydrocarbon fraction mainly contains butene-1 and butenes-2, isobutene, isobutane, n-butane, as well as a small amount of butadiene-1,3. This fraction is the so-called olefinic fraction because the proportion of olefins (isobutene, butene-1 and butenes-2) that it contains is larger than its proportion of paraffins (isobutane, n-butane). It is most often sent into an alkylation installation that adds the mixture of butenes (isobutene, butene-1 and butenes-2) to the isobutane. As the stoichiometry of the alkylation requires one mol of isobutane per mol of butene, the isobutane content of the fraction that comes from cracking is most generally inadequate for alkylating all of the olefins of this fraction; an outside supply of isobutane is necessary. This importation can be difficult and at the very least expensive.

It is known that it is possible to increase selectively the isobutane concentration of the olefinic hydrocarbon fraction of 4 carbon atoms sent to an alkylation unit. The applicant thus has already described, in French Patent 2,436,176 (to which U.S. Pat. No. 4,268,701 corresponds), a process that comprises:

1. The hydro-isomerization of butene-1 of a C4 olefinic fraction to obtain a C4 fraction that is enriched with butenes-2 and that is low in butene-1, whereby the isomerization of butene-1 accompanies the selective hydrogenation of the butadiene-1,3 that is present;
2. the fractionation of the C4 fraction that is thus obtained to obtain separately an isobutane- and isobutene-enriched fraction and a butenes-2-enriched fraction;
3. the hydrogenation of the isobutane- and isobutene-enriched fraction to convert at least a portion of the isobutene into isobutane and thus to increase the content of the latter; and
4. the alkylation of the butenes-2-enriched fraction with the fraction with an increased isobutane content.

The alkylation product is sent into a stabilization zone, where the final alkylate is separated at the bottom, and the non-transformed C4 hydrocarbons (mainly isobutane) are separated at the top.

The sequence of these operations offers many advantages. The most reactive compound, namely butadiene-1,3, is hydrogenated and will not produce parasitic reactions in the alkylation operation, namely the formation of muds or oils that, in addition to the elimination problem that it poses, brings about excessive acid consumption (sulfuric acid or hydrofluoric acid).

Furthermore, the hydro-isomerization of butene-1 into butenes-2 makes it possible to separate the isobutene (boiling point: −6.9° C.) from butenes-2 (boiling point of butene-2 trans: +9° C.; of butene-2 cis: +3.7° C.) and therefore makes it possible to hydrogenate mainly isobutene into isobutane, while retaining the butenes-2. A mixture (almost stoichiometric or with excess isobutane) that makes it possible to maximize production of the alkylation unit thus is prepared.

Moreover, the characteristics of the alkylate that is produced, namely the "research" and "motor" octane numbers, are considerably improved, regardless of the alkylation process, when the butenes-2 are used as olefins. Thus, in the case of alkylation with sulfuric acid or with hydrofluoric acid, the octane numbers are considerably improved, as Table 1 shows below:

TABLE 1

|  | Butene-1 | | Butenes-2 | | Isobutene | |
| --- | --- | --- | --- | --- | --- | --- |
|  | HF | $H_2SO_4$ | HF | $H_2SO_4$ | HF | $H_2SO_4$ |
| IOR* | 90–91 | 97–98 | 96–97 | 97–98 | 94–95 | 90–91 |
| IOM* | 88–89 | 93–94 | 92–93 | 93–94 | 91–92 | 88–89 |

*IOR designates the "research" octane number, and IOM designates the "motor" octane number.

Actually, it is seen that the octane numbers of the "sulfuric" alkylate of isobutene are very considerably lower than those of the "sulfuric" alkylate of the n-butenes, while the octane numbers of the "hydrofluoric" alkylate of butene-1 are very considerably lower than those of the "hydrofluoric" alkylate of butenes-2. The almost-exclusive presence of butenes-2 in the alkylation feedstock therefore makes it possible, both in the case of "sulfuric" alkylation and in that of the "hydrofluoric" alkylation, to obtain maximum octane number values.

It has now been discovered that it was possible also to improve the production of aliphatic alkylate from a C4 catalytic cracking or steam-cracking fraction.

The process of the invention calls for diluting the feedstock of the hydrogenation zone by the top effluent (that mainly contains isobutane) from the separation zone (stabilization) that is located downstream from the alkylation unit. Actually, the hydrogenation reaction is exothermic, and it is necessary to control the rise in temperature in the hydrogenation reactor if maintaining control is desired. Generally, the isobutane that is thus recycled corresponds to 5 to 10 times the amount of isobutene. The isobutene that is thus diluted can thus be hydrogenated almost completely with an acceptable temperature increase (ΔT) that is generally less than 50° C. This way of proceeding is very advantageous, because it makes it possible to simplify the installation of hydrogenation by avoiding the necessity to increase the recycling capacity of the hydrogenated product to the hydrogenation reactor, which would involve providing a larger reservoir and one (or more) additional pump(s).

Generally, the invention proposes an improved process for preparing an aliphatic alkylate with a high octane number from a C4 catalytic cracking or steam-cracking fraction that contains mainly butene-1, butenes-2, isobutene, isobutane, n-butane, as well as a small amount of butadiene-1,3, whereby this process comprises:

(a) The hydro-isomerization of said C4 fraction that has the result of obtaining a mixture that contains for the most part butenes-2, isobutene and isobutane;
(b) the separation, by distillation of the hydro-isomerized fraction, of a butene-2-rich effluent that is collected at the bottom and an isobutane- and isobutene-rich effluent that is collected at the top;
(c) the sending of said isobutene- and isobutane-rich effluent into a hydrogenation zone that produces an effluent that for the most part contains isobutane;
(d) the sending of said butenes-2-rich effluent that is derived from stage (b) and of said effluent that for the most part contains the isobutane that is derived from stage (c) into an alkylation zone that produces, by the addition of isobutane to butenes-2, an isooctane mixture that contains excess isobutane; and (e) the separation by distillation of excess isobutane, which comes out at the top, and alkylate with an improved octane number, which comes out at the bottom; whereby this process is characterized by the fact that it also comprises (f) the recycling of the excess isobutane that is recovered in stage (e) upstream from hydrogenation stage (c) of the top effluent from the distillation of stage (b) (whereby said effluent comprises isobutane, isobutene and residual butene-1) so as to dilute the latter.

The process of the invention as defined above is depicted diagrammatically by the accompanying figure, where the different stages can be described as follows.

The $C_4$ hydrocarbon fraction is introduced via pipe 1 into hydro-isomerization unit R1, in which hydrogen is also introduced. This unit carries out the hydrogenation of the butadiene-1,3 that is present in a small amount and the isomerization of butene-1 into butenes-2. The product of this unit is then introduced via pipe 2 into distillation column C1, which separates, at the bottom, the butenes-2-rich effluent that is sent via pipe 3 to alkylation unit R3, and, at the top, the isobutene and isobutane-rich effluent that is sent via pipe 4 to hydrogenation unit R2 that also receives hydrogen. This unit produces an isobutane-rich effluent that is then directed via pipe 5 to alkylation unit R3. The crude alkylate that contains a large excess of isobutane is sent via pipe 6 into distillation column C2, in which the final alkylate that comes out at the bottom via pipe 8 is separated; the top effluent that mainly consists of excess isobutane is recycled via pipe 7 to supply pipe 4 of isobutene hydrogenation unit R2.

The preferred operating conditions of the different stages of the process of the invention are as follows.

Stage (a) (zone R1), the hydro-isomerization comprises the isomerization of butene-1 into butenes-2 and simultaneously the selective hydrogenation of the butadiene-1,3 that is present in a small amount in the initial C4 fraction. These reactions can be carried out with various specific catalysts that comprise one or more metals, for example from group 10 of the periodic table (Ni, Pd and/or Pt), that is (are) deposited on a substrate. Preferably used is a catalyst that comprises at least one compound of palladium or nickel that is fixed on a refractory mineral substrate, for example on an alumina. The palladium or nickel content on the substrate can consist of between 0.01 and 5% by weight, preferably between 0.05 and 1% by weight. Various pretreatment methods that are known to one skilled in the art optionally can be applied to these catalysts to improve the selectivity in the hydrogenation of butadiene-1,3 into butenes, at the expense of the total hydrogenation of butane that it is necessary to avoid. Thus, it is possible to sulfurize these catalysts. Advantageously, a catalyst that comprises palladium that is deposited on alumina and that preferably contains 0.05 to 10% by weight of sulfur is used.

The sulfurizing of the catalyst can be carried out in situ (in the reaction zone), or even better, ex situ. In the latter case, the operation is advantageously performed according to the process that is described in the published French Patent Applications FR-A-2 708 596 and 2 708 597, which provide the treatment of the catalyst before it is loaded into the hydrogenation reactor by at least one sulfur compound that is diluted in a solvent, loading into the reactor the catalyst that is obtained and that contains 0.05 to 10% by weight of sulfur, and its activation under a neutral or reducing atmosphere at a temperature of between 20 and 300° C., pressure between 0.1 and 5 MPa and a VVH of between 50 and 600 $h^{-1}$, whereby the feedstock is then brought into contact with said activated catalyst.

The use of the catalyst, preferably with palladium, is not critical, but it is generally preferred to use at least one down-flow reactor through a fixed catalyst bed. When the butadiene-1,3 proportion in the fraction is large, which is the case, for example, of a steam-cracking fraction when it is not desired to extract from it butadiene-1,3 for specific uses, it may be advantageous to carry out the transformation in two reactors in series to better monitor the selectivity of the hydrogenation. The second reactor can then have a rising flow and play a finishing role.

The amount of hydrogen that is necessary to all of the reactions that are carried out in this stage is adjusted based on the composition of the fraction to advantageously have only a slight excess of hydrogen relative to the theoretical stoichiometry.

The operating conditions are selected in such a way that the reagents and the products are in a liquid phase. It may be advantageous, however, to select an operating mode such that the products are partially evaporated at the outlet of the reactor, which facilitates the thermal monitoring of the reaction. The temperature may vary from 20 to 200° C., preferably from 50 to 150° C., or even better, from 60 to 150° C. The pressure can be adjusted between 0.1 and 5 MPa, preferably between 0.5 and 4 MPa and advantageously between 0.5 and 3 MPa, such that the reagents are at least partially in a liquid phase. The volumetric flow rate can be between 0.5 and 10 $h^{-1}$ and preferably between 1 and 6 $h^{-1}$, with an $H_2$/butadiene molar ratio of 0.5/1 to 5/1, preferably 1/1 to 3/1.

The effluent that is obtained for the most part contains isobutane and isobutene, some butenes-2, very little butene-1 and it no longer contains butadiene-1,3.

Separation stage (b) is carried out in a distillation zone (in particular a column that is to be distilled that comprises 5 to 200 theoretical plates) that operates between 0.3 and 1 MPa with a reflux rate (reflux/distillate) of 5/1 to 20/1. A top effluent that comprises isobutane, isobutene and residual butene-1 of stage (a) and a bottom effluent that comprises n-butane and butenes-2, which will be sent into stage (d) in an alkylation zone with sulfuric acid or with hydrofluoric acid, are obtained.

In stage (c) (zone R2), almost total hydrogenation of the isobutene and residual butene-1 of the top effluent is carried out from the separation of stage (b), through passage of the latter, at least partially in a liquid phase, on a catalyst that comprises one or more metals, for example from group 10 of the periodic table (Ni, Pd and Pt) that are deposited on a substrate. Preferably used is a catalyst that comprises at least one palladium compound that is fixed on a refractory substrate, for example on an alumina; the palladium content on the substrate can be between 0.01 and 5% by weight, preferably between 0.05 and 1% by weight.

The catalyst is loaded into a reactor generally in its oxidized form (PdO) and is therefore to undergo a reduction treatment under a gas stream that contains hydrogen of between 20 and 200° C., a pressure of between 0.1 and 5 MPa and an hourly gas flow rate per catalyst volume unit of between 50 and 600 $h^{-1}$. The feedstock is then brought into contact with the catalyst that is thus activated. The reactor that is used is sized according to the general rules that are known to one skilled in the art. Generally at least one down-flow reactor that comprises a fixed catalyst bed is used.

The amount of hydrogen that is necessary for all of the reactions that are carried out in this stage is adjusted based on the composition of the fraction for advantageously having only a slight excess of hydrogen relative to the stoichiometry. As for stage (a), the operating conditions are selected in such a way that the reagents and the products are in a liquid phase. It may be advantageous, however, to select an operating mode such that the products are partially evaporated at the outlet of the reactor, which facilitates the thermal monitoring of the reaction. The temperature can vary from 20 to 200° C., preferably from 50 to 150° C., or even better, from 60 to 150° C. The pressure can be adjusted between 0.1 and 5 MPa, preferably between 0.5 and 4 MPa and advantageously between 0.5 and 3 MPa, in such a way that the reagents are at least partially in a liquid phase. The volumetric flow rate can be between 0.5 and 10 h$^{-1}$ and preferably between 1 and 6 h$^{-1}$, with an H$_2$/isobutene molar ratio of 0.1/5 to 5/1, preferably from 1/1 to 2/1.

An effluent that contains, for the most part, isobutane that is sent in stage (d) to the alkylation zone with sulfuric acid or with hydrofluoric acid is obtained.

In stage (d), the isobutane-rich fraction that comes from hydrogenation unit R2 is then sent to alkylation installation R3, where it is reacted with the butenes-2-rich fraction to form the crude alkylate. In general, it is used as a sulfuric acid or hydrofluoric acid catalyst. Mentioned as prior art will be, among others, U.S. Pat. Nos. 2,308,560, 2,320,199, 2,429,205, 2,768,987, 2,818,458, 2,914,592, 2,920,124, 2,429,205 and 3,855,344. The invention is not limited in any way to special conditions of the alkylation reaction that are well known.

In stage (e), the crude alkylate is sent to distillation zone C2.

In stage (f), the feedstock of the reactor is diluted by the isobutane that is obtained from separation column C2 that is located downstream from alkylation unit R3. The hydrogenation reaction is actually exothermic, and the monitoring of the temperature increase in the reactor is necessary if maintaining control is desired. Generally, the thus recycled isobutane corresponds to 5 to 10 times the amount of isobutene. The thus diluted isobutene can than be hydrogenated almost completely with an acceptable temperature increase that is generally less than 50° C. This way of proceeding is very advantageous, because it makes it possible to simplify the installation of hydrogenation by avoiding the necessity to increase the recycling capacity of the hydrogenated product toward the hydrogenation reactor, which would involve providing a larger reservoir and one (or more) additional pump(s).

The following example illustrates the invention without limiting its scope.

BRIEF DESCRIPTION OF THE DRAWING

The drawing represents a schematic flowsheet of an embodiment of the process of the invention described in detail in the Example, wherein streams referred to as "Flow #" are referenced with respect to the drawing.

EXAMPLE

A fraction C4 that is obtained from catalytic cracking and that has the composition that is indicated in Table 2 (flow 1) is introduced continuously into a hydro-isomerization installation with a flow rate per unit of mass that is indicated in Table 2 and under a pressure of 2 MPa in a reactor that comprises a fixed bed of 13 tons of a catalyst that consists of palladium (0.3% by weight) on alumina, previously sulfurized and then reduced under a hydrogen flow to a temperature of 200° C. for 8 hours. Pure hydrogen is also injected, as indicated in Table 2. The temperature, which is 70° C. at the inlet, rises to 89° C. at the outlet. The effluent from the reactor (flow 2), which has the composition that is indicated in Table 2, is sent into a distillation column that comprises 80 distillation plates. This column operates at a pressure of 0.65 MPa and a top temperature of 44° C.; the reflux rate that is expressed by the ratio between the reflux rate and that of the distillate (R/D) is 10. The butenes-2-rich product that is drawn off at the bottom has the composition that is indicated in Table 2 (flow 3). The isobutene- and isobutane-rich distillate, whose composition is indicated in Table 2, is mixed with a rich flow of isobutane that is obtained from column C2 that is to be distilled and that follows the alkylation unit; its composition is indicated in Table 2 (flow 7). The mixture of the two flows above constitutes the feedstock of hydrogenation unit R2 from isobutene into isobutane, whose composition is given in Table 2 (flow 4). This feedstock is introduced continuously at a flow rate per unit of mass that is indicated in Table 2 and under a pressure of 1.95 MPa in hydrogenation installation R2, which consists of a reactor that comprises a fixed bed of 10 tons of a catalyst that consists of palladium (0.3% by weight) previously reduced under a hydrogen flow to 100° C. for 4 hours. Pure hydrogen is also injected as indicated in Table 2. The temperature, which is 50° C. at the inlet, rises to 96° C. at the outlet. The effluent from the reactor has the composition that is indicated in Table 2 (flow 5). It is seen that it contains in large part isobutane (close to 87%).

This effluent is sent to alkylation installation R3, in which it is mixed with butenes-2-rich flow 3. In alkylation installation R3, the butenes-2 are almost totally converted into isooctanes (flow 6) by the addition of isobutane. This crude alkylate is sent into column C2 that is to be distilled in which the final alkylate that constitutes a gasoline with high octane numbers ("research" and "motor") is separated at the bottom, and flow 7, whose composition is given in Table 2, is separated at the top.

Flow 7 is, as indicated above, mixed with isobutane- and isobutene-rich distillate from column C1, and sent to hydrogenation unit R2.

TABLE 2

| Component (% by weight) | Hydro-isomerization feedstock (flow 1) | H2 hydro-isomerization gas | Hydro-isomerization effluent (flow 2) | Butenes-2-rich-effluent (flow 3) | Isobutane- and isobutene-rich effluent (flow 4) | Isobutane recycling (flow 7) | Isobutene hydrogenation feedstock (flows 4–7) | H$_2$ gas from isobutene hydrogenation | Effluent from isobutene hydrogenation (flow 5) |
|---|---|---|---|---|---|---|---|---|---|
| Propane | 0.27 | | 0.27 | | 0.63 | 2.3 | 1.92 | | 1.90 |
| Isobutane | 20.00 | | 20.00 | | 46.34 | 86.4 | 77.20 | | 86.89 |
| Butene-1 | 14.12 | | 2.82 | 0.23 | 6.23 | | 1.43 | | 0 |
| Isobutene | 21.22 | | 21.20 | 1.76 | 46.80 | | 10.75 | | 1.07 |

TABLE 2-continued

| Component (% by weight) | Hydro-isomerization feedstock (flow 1) | H2 hydro-isomerization gas | Hydro-isomerization effluent (flow 2) | Butenes-2-rich-effluent (flow 3) | Isobutane- and isobutene-rich effluent (flow 4) | Isobutane recycling (flow 7) | Isobutene hydrogenation feedstock (flows 4–7) | H$_2$ gas from isobutene hydrogenation | Effluent from isobutene hydrogenation (flow 5) |
|---|---|---|---|---|---|---|---|---|---|
| n-butane | 9.97 | | 10.93 | 19.23 | | 11.1 | 8.55 | | 9.99 |
| Butenes-2 | 30.80 | | 42.39 | 74.58 | | | | | |
| Butadiene-1,3 | 1.23 | | 0 | 0 | | | | | |
| Total C$_5$ | 2.39 | | 2.39 | 4.20 | | 0.2 | 0.15 | | |
| TOTAL | 100 | | 100 | 100 | 100 | 100 | 100 | | 100 |
| Hydrogen | | 99.99 | | | | | | 99.99 | |
| Methane | | 0.01 | | | | | | 0.01 | |
| H$_2$ flow rate (kg/h) | | 28 | 0 | | | | | 263.4 | |
| C$_4$ flow rate (kg/h) | 35313 | | 35341 | 20088 | 15253 | 51152 | 66405 | | 66668.4 |

If the composition of flow 4 and that of flows 4+7 (after flow 7 is recycled) are considered, it is seen that the isobutene concentration of the flow that is to be hydrogenated rises from 46.80% by weight to 10.75% by weight.

At the outlet of the hydrogenation reactor (flow 5), the isobutene concentration is 1.07% by weight, which corresponds to a conversion of the isobutene of $$\frac{10.75 - 1.07}{10.75} \times 100 = 90\%.$$

If flow 4 were hydrogenated (without dilution by flow 7) for the same residual isobutene content, the conversion of isobutene should be $$\frac{(46.80 - 1.07)}{46.80} \times 100 = 98\%,$$

which would require more severe conditions.

In addition, because of the dilution of the isobutene in the feedstock that is to be hydrogenated (in the case of the recycling of flow 7), the increase in the temperature in the hydrogenation reaction would be easier to control than in the absence of such a recycling.

Finally, if it is considered that for normal operation of a hydrogenation reaction the isobutene content at the inlet of the reactor should be brought to about 5% by weight by a recycling of the hydrogenation effluent, in this example, whereby the concentration of the isobutene in the feedstock that is to be hydrogenated (flows 4+7) are 10.75% by weight, a recycling rate of the hydrogenation effluent of about 1/1 relative to the feedstock will be adequate.

If dilution of feedstock 4 by flow 7 had not been used, the isobutene concentration of 46.80% by weight would have required a recycling rate of the hydrogenation effluent of about 9/1 relative to the feedstock.

A recycling rate that is decreased to 1/1 makes it possible to reduce significantly the power of the recycling pumps that are to be installed.

What is claimed is:

1. A process for the preparation of an aliphatic alkylate from a C4 catalytic cracking or steam-cracking fraction that contains n-butane, isobutane, isobutene, butene-1 and butenes-2, as well as butadiene-1,3, said process comprising:
    (a) hydro-isomerizing said C4 fraction obtaining a mixture that contains butenes-2, isobutene and isobutane;
    (b) separating by distillation of the hydro-isomerized fraction from (a), a butene-2-rich bottom effluent and an isobutane- and isobutene-rich top effluent;
    (c) hydrogenating said isobutene- and isobutane-rich effluent producing an effluent that contains isobutane;
    (d) alkylating said butenes-2-rich effluent that is obtained from (b) with said effluent containing isobutane obtained from (c) producing by the addition of isobutane to butenes-2, an isooctane mixture that contains unreacted excess isobutane;
    (e) separating the isooctane mixture that contains excess isobutane by distillation into a top product containing excess isobutane and a bottom product containing an alkylate containing isooctane; and
    (f) recycling excess isobutane recovered in (e) to the top effluent from distillation (b) upstream from hydrogenation (c).

2. A process according to claim 1 wherein said separation (b) is carried out in a column that comprises from 5 to 200 theoretical plates and that operates between 0.3 and 1 MPa with a reflux/distillate rate of 5/1 to 20/1.

3. A process according to claim 1, comprising in (c) hydrogenating the top isobutane- and isobutene-rich effluent from distillation (b) by contacting said effluent at least partially in liquid phase with a catalyst that comprises at least one of nickel, palladium or platinum in such a way as to obtain an effluent that contains isobutane.

4. A process according to claim 1, wherein in (d), the alkylation is catalyzed by sulfuric acid or hydrofluoric acid.

5. A process according to claim 1, comprising in (a), selectively hydrogenating butadiene-1,3 and isomerizing butene-1 to butenes-2 by contacting said C4 fraction in liquid phase with a catalyst that comprises at least one of nickel, palladium or platinum in such a way as to obtain an effluent that contains a major amount of isobutane and isobutene, a minor amount of butenes-2 and butene-1, and that no longer contains butadiene-1,3.

6. A process according to claim 5, wherein the catalyst is deposited on a substrate.

7. A process according to claim 5, wherein (a) is conducted at 20 to 200° C., a pressure of 1 to 5 MPa, a volumetric flow rate of 0.5 to 10 h$^{-1}$, and an H$_2$/butadiene molar ratio of 0.5/1 to 5/1.

8. A process according to claim 3, wherein (c) the catalyst is deposited on a substrate.

9. A process according to claim 3, wherein (c) is conducted at 20 to 200° C., a pressure of 0.1 to 5 MPa, a volumetric flow rate of 0.5 to 10 $h^{-1}$, and an $H_2$/olefin molar ratio of 0.5/1 to 5/1.

10. A process according to claim 1, further comprising blending the effluent that no longer contains butadiene-1,3 with a gasoline.

11. In a process for the preparation of an aliphatic alkylate from a fraction containing n-butane, isobutane, isobutene, butene-1, butenes-2 and butadiene-1,3 by isomerizing butenes-1 to butenes-2, hydrogenating isobutene to isobutane and alkylating butene-2 with isobutane, the improvement comprising separating unreacted isobutane from the resulting aliphatic alkylate and recycling the isobutane to hydrogenation.

12. A process according to claim 11, further comprising blending the aliphatic alkylate with a gasoline.

* * * * *